United States Patent [19]

Yamazaki et al.

[11] Patent Number: 4,826,893

[45] Date of Patent: May 2, 1989

[54] DENTAL RESIN COMPOSITION

[75] Inventors: Noboru Yamazaki, Tokyo; Akira Yamanaka, Yokohama; Shigeaki Kurata, Tokyo, all of Japan

[73] Assignee: G-C Dental Industrial Corp., Tokyo, Japan

[21] Appl. No.: 142,244

[22] Filed: Jan. 5, 1988

Related U.S. Application Data

[63] Continuation of Ser. No. 842,918, Mar. 24, 1986, abandoned.

[30] Foreign Application Priority Data

Apr. 2, 1985 [JP]  Japan .................................. 60-68532

[51] Int. Cl.$^4$ .............................................. C08L 83/06
[52] U.S. Cl. .................................... 523/115; 523/116; 525/100; 525/479; 525/102
[58] Field of Search ................. 526/279; 525/479; 523/109, 115, 116

[56] References Cited

U.S. PATENT DOCUMENTS

| | | | |
|---|---|---|---|
| 3,575,910 | 4/1971 | Thomas | 525/479 |
| 4,413,104 | 11/1983 | Deubzer et al. | 525/479 |
| 4,504,231 | 3/1985 | Koblitz et al. | 523/116 |

*Primary Examiner*—Wilbert J. Briggs, Sr.
*Attorney, Agent, or Firm*—Oblon, Fisher, Spivak, McClelland & Maier

[57] ABSTRACT

A dental resin composition comprising (a) a siloxane polymer obtained by polymerizing an oligomer comprising (I) a silane compound containing therein an ethyleneically unsaturated group having bonded thereto (II) a silane compound containing therein a phenyl group or an alkyl group, (b) a monomer copolymerizable with said siloxane polymer (a), and (c) a polymerization catalyst, and optionally, (d) a filler, is disclosed. The dental resin composition of the invention is markedly improved in physical properties such as compressive strength, bending strength, abrasion resistance, and water sorption and therefore, it is quite useful as a denture base resin, a crown and bridge resin, and a filling resin in the dentistry.

22 Claims, No Drawings

DENTAL RESIN COMPOSITION

This application is a Continuation of application Ser. No. 842,918, filed on Mar, 24, 1986, now abandoned.

FIELD OF THE INVENTION

The present invention relates a novel dental resin composition comprising a blend of a siloxane polymer having a stiff ladder structure and having a polymerizable ethylenically functional group and a hydrophobic group in the side chain of the same molecule thereof and an Si—O bond in the main chain thereof with a copolymerizable monomer, said resin composition after polymerization being markedly improved in physical properties such as compressive strength, bending strength, abrasion resistance, water sorption etc.

BACKGROUND OF THE INVENTION

Methyl methacrylate-based materials which have hitherto been widely used as a denture base resin, a crown and bridge resin, or a filling resin have excellent advantages in operability, esthetics, stability in the oral conditions, etc. On the other hand, since these materials are poor in mechanical strengths, they have drawbacks in terms of strength such that, for example, in the preparation of a denture, after polymerization in a gypsum mold by the usual manner, it is broken when dug out from a flask, the denture is broken when dropped inadvertently, and that in the case that the denture is set in the mouth, it is broken when biting.

Taking into account the temperature feeling, sense of taste and extraneous feeling when set, it is desirable that the denture is as thin as possible. However it is actually impossible to render it thin from the standpoint of its strength. Further, when used as the crown and bridge resin, because of its poor abrasion resistance, there is a fear that the labial surface have wear off by brushing, etc. or the incisal edge thereof is broken.

In order to remove these drawbacks, some attempts to improve the mechanical strengths from the viewpoint of formulation have been made. For example, in denture base materials of a powder-liquid type, a method for adding as a crosslinking agent an aliphatic, di- to tetrafunctional methacrylic acid ester-based monomer to the formulation solution is generally employed. The addition of such a crosslinking agent improves the hardness and abrasion resistance to a some extent, but it renders the material brittle to thereby reduce the bending strength. Further, if a large quantity of the crosslinking agent is added, not only the adhesion to the resin tooth is reduced, but also the denture which has been highly crosslinked after the polymerization cannot be repaired by a cold-curing resin. As the powdery polymer, those which are intended to be improved in the physical properties by incorporating a copolymer of methyl methacrylate and vinyl chloride or styrene are commercially available, but they are not always expected to be greatly improved in the hardness and bending strength. Still further, as the liquid component of the crown and bridge resin, difunctional or higher functional methacrylic acid ester-based monomers are in general widely used. In this case, the abrasion resistance upon which the crown and bridge resin using methyl methacrylate is poor is improved, but the toughness and bending strength become lowered to cause a breakage of the incisal edge.

SUMMARY OF THE INVENTION

An object of the present invention is to improve the drawbacks of the prior art techniques. That is, the present invention relates to a dental resin composition comprising a blend of a siloxane polymer having a stiff ladder structure and having a polymerizable ethylenically functional group and a hydrophobic group in the side chain of the same molecule thereof and an Si—O bond in the main chain thereof with a copolymerizable monomer, said resin composition after polymerization being markedly improved in physical properties such as compressive strength, abrasion resistance, bending strength, water sorption, etc., without causing any harm in the inherent advantages of methyl methacrylate-based materials which have hitherto been used as a denture base resin, a crown and bridge resin, or a filling resin, such as operability, esthetics, stability in the oral conditions, and easy to repair.

DETAILED DESCRIPTION OF THE INVENTION

In the present invention, though the siloxane polymer is preferred to have a ladder structure soluble in the copolymerizable monomer, it may be a three-dimensionally condensed polymer which is soluble in the copolymerizable monomer, a partially gelled polymer, or a polymer which swells in the copolymerizable monomer.

The resin composition of the present invention is a composition comprising a polymerizable siloxane polymer having a polymerizable ethylenically unsaturated functional group and a hydrophobic group in the same polymer and a copolymerizable monomer blended with a polymerization catalyst, and it is polymerized by the usual method in the dentistry. The polymerizable functional group is bonded to the monomer to form a tough three-dimensional network structure, to thereby contribute to marked improvements in bending strength, abrasion resistance, hardness, compressive strength, etc. Further, in the present invention, the above-described polymerizable siloxane polymer, monomer and polymerization catalysts are essential, but if desired, a filler may be further incorporated.

A silane compound (I) which is used as a starting material for the synthesis of the siloxane polymer (a) is a compound represented by the following general formula:

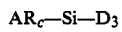

AR$_c$—Si—D$_3$ wherein D represents a hydrolyzable group; R represents an alkylene group containing from 1 to 4 carbon atoms; c is an integer of 0 or 1; and A represents

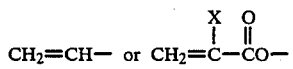

$$CH_2=CH- \text{ or } CH_2=\overset{X}{\underset{|}{C}}-\overset{O}{\underset{\|}{C}}O-$$

in which X represents a hydrogen atom or a hydrocarbon group containing from 1 to 6 carbon atoms.

In the above general formula, any hydrolyzable group can be used as D, and examples thereof include Cl, methoxy, ethoxy, propoxy, and isopropoxy. R is a divalent alkylene group containing from 1 to 4 carbon atoms, which is bonded to the silicon atom, and examples thereof include methylene, ethylene, and propylene. c is 0 or 1, and R may be absent. When c is 0, then A is CH$_2$=CH—. When A is

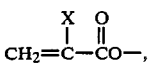

X is a hydrocarbon group containing from 1 to 6 carbon atoms, and in this case, an ester group is present in the compound. Examples of X include methyl, ethyl, isopropyl, and butyl.

Thus, suitable examples of the silane compound (I) include γ-methacryloxypropyl trimethoxysilane, γ-methacryloxypropyl triethoxysilane, vinyl triethoxysilane, vinyl tris(β-methoxyethoxy)silane, vinyl trichlorosilane, etc., with the γ-methacryloxypropyl trimethoxysilane being most preferred.

A silane compound (II) is a compound represented by the following general formula:

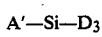

wherein D represents a hydrolyzable group, and A' represents

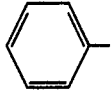

or an alkyl group containing from 1 to 9 carbon atoms.

In the above general formula, any hydrolyzable group can be used as D. A' is

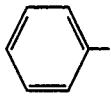

or an alkyl group containing from 1 to 9 carbon atoms, which is bonded to the silicon atom.

Thus, suitable example of the silane compound (II) include phenyl trimethoxysilane, phenyl triethoxysilane, methyl trimethoxysilane, ethyl trimethoxysilane, n-propyl trimethoxysilane, n-butyl trimethoxysilane, phenyl trichlorosilane, methyl trichlorosilane, ethyl trichlorosilane, n-propyl trichlorosilane, n-butyl trichlorosilane, etc. Among them, the phenyl triethoxysilane is preferred from the standpoint of hydrophobicity.

Next, the synthesis of an oligomer from the aforesaid silane compounds is explained. In the synthesis of an oligomer, a hydrolysis reaction at room temperature was employed. That is, the silane compound (I) and the silane compound (II) were added in a prescribed molar percentage proportion to a tetrahydrofuran solvent under an acidic condition with hydrochloric acid, and water in an amount of 3 molar times that of the silane compounds was further added thereto, whereby the reaction was completed by hydrolysis for 24 hours. The reaction product was washed with a saturated aqueous solution of sodium chloride to remove off the hydrochloric acid, and the tetrahydrofuran was distilled off under a reduced pressure by means of an evaporator. There was thus obtained an oligomer.

The synthesis of a siloxane polymer (a) from the oligomer is explained. The siloxane polymer (a) was synthesized from the oligomer by a condensation reaction. That is, the oligomer was added to a toluene (or xylene) solvent, and a dehydrating agent (N,N'-dicyclohexylcarbodiimide) in an amount of 2 molar times that of the oligomer was further added thereto, whereby the synthesis was completed by reaction at from 130 to 160° C. for 5 hours. The by-products obtained by the dehydrating agent were filtered out, and reprecipitation was carried out in a methanol solution. There was thus obtained the siloxane polymer (a).

With respect to the molar percentage proportion of the silane compound (I) to the silane compound (II), the silane compound (I) can be used within the range of from 1 to 50 mol%. If the amount of the silane compound (I) exceeds 50 mol%, the resulting siloxane polymer (a) exhibits a gelled state in which the self-crosslinking occurs and becomes a polymer insoluble in the monomer. On the other hand, if the amount of the silane compound (I) is less than 1 mol%, a dental resin composition composed of the resulting siloxane polymer takes place the phase separation after the curing and becomes a turbid and opaque resin polymer which is no longer suitable for practical uses. Thus, the silane compound (I) is used in an amount of from 1 to 50 mol% and preferably from 5 to 30 mol%.

Suitable examples of a monomer (b) include methyl methacrylate, ethyl methacrylate, ethylene glycol dimethacrylate, diethylene glycol dimethacrylate, triethylene glycol dimethacrylate, tetraethylene glycol dimethacrylate, 1,3-butanediol dimethacrylate, neopentyl glycol dimethacrylate, trimethylolpropane trimethacrylate, 2,2-bis(4-methacryloxyphenyl)propane, 2,2-bis(4-methacryloxypolyethoxy)phenylpropane, 1,3-bis(methacryloxyethoxy)benzene, etc. Among them, the methyl methacrylate is preferred for the use in the denture base resin, and the 2,2-bis(4-methacryloxypolyethoxy)phenylpropane is preferred for the use of the crown and bridge resin.

With respect to the proportion of the siloxane polymer (a) to the polymerizable monomer (b), the siloxane polymer (a) can be used within the range of from 1 to 50% by weight. If the amount of the siloxane polymer (a) is less than 1% by weight, there is not found a meaningful difference in the bending strength of the resulting polymerized resin from that of a polymerized resin having no siloxane compound added thereto (1682 kg/cm$^2$, see Comparative Example A-11). On the other hand, when the amount of the siloxane polymer (a) is 50% by weight, the resulting polymerized resin has a bending strength of 1795 kg/cm$^2$ (see Example A-3) which is higher than that of the polymerized resin having no siloxane compound added thereto. But if the amount of the siloxane compound (a) exceeds 50% by weight, the physical properties tend to become rather lowered. Accordingly, the siloxane polymer (a) can be used in an amount of from 1 to 50% by weight, but taking into account a marked improvement in bending strength and operability, it is preferably used in an amount of from 5 to 40% by weight.

As a polymerization catalyst (c), polymerization initiators such as organic peroxides (e.g, benzoyl peroxide, lauryl peroxide and cumene hydroperoxide) and azo compounds (e.g., 2,2'-azobisisobutyronitrile) can be used. Among them, the benzoyl peroxide is preferred. The organic peroxide may be used in combination with as a polymerization promotor a tertiary amine such as dimethyl-p-toluidine and 2-hydroxyethyl-p-toluidine. In this case, in order that the both are in a non-contact state, it is necessary that a composition to which the organic peroxide has been added is preserved separately from a composition to which the tertiary amine has been added and that the both are mixed when used. A suitable amount of the tertiary amine added is in the range of from 0.5 to 5% by weight, and a suitable amount of the organic peroxide is in the range of from 0.1 to 5% by weight. In the case that a composition to which less than 0.5% by weight of the tertiary amine has been added is mixed with a composition to which less than 0.1% by weight of the organic peroxide has been added, the curing is not satisfactory. On the other hand, if the amount of each of the tertiary amine and organic peroxide exceeds 5% by weight, there is caused a problem in pot life, and the cured resin tends to be colored yellow.

Suitable examples of a filler (d) include inorganic fillers such as borosilicate glass, quartz, feldspar, amorphous silica, alumina, and aluminosilicate and organic fillers such as polymethyl methacrylate and a copolymer of methyl methacrylate and a methacrylic acid ester. These inorganic fillers and organic fillers can be used either alone or in admixture. Further, a so-called organic composite filler in which an inorganic filler is coated with an organic polymer can be used.

EXAMPLES

The Examples of the present invention were carried out under a common condition as set forth below, and the results obtained are summarized in the tables for sake of easiness in comparison.

COMMON CONDITION

A Common Condition of Examples A-1 to A-10 and Comparative Examples A-11 to A-12

A powder of polymethyl methacrylate (granularity: 120–150 Tyler mesh) containing 0.2 wt % benzoyl peroxide was used as a filler, and a formulation solution of each of the Examples was mixed with the powder in a mixing ratio of 1:2 (by weight) to prepare a dough. The dough was preliminarily polymerized at 70° C. for 30 minutes and then polymerized really at 100° C. for 30 minutes according to the usual manner in the dentistry, followed by finishing into a prescribed size for sample.

B Common Condition of Examples B-1 to B-10 and Comparative Examples B-11 to B-12

A powder of polymethyl methacrylate (granularity: 120–150 Tyler mesh) to which 1.0 wt % of benzoyl peroxide had been added was used as a filler, and a formulation solution of each of the Examples was mixed with the powder in a mixing ratio of 3:5 (by weight) to prepare a dough. The dough was polymerized in a pressure pot filled with warm water at 45° C. under a pressure of 2.5 kg/cm² for 20 minutes by the usual manner, followed by finishing into a prescribed size for sample.

C Common Condition of Examples C-1 to C-9 and Comparative Example C-10

A powder of polymethyl methacrylate (granularity: 250 Tyler mesh pass) containing 0.3 wt % benzoyl peroxide was used as a filler, and a formulation solution of each of the Examples was mixed with the powder in a mixing ratio of 5:3 (by weight) to prepare a dough. The dough was preliminarily polymerized at 130° C. and then polymerized really at 150° C. for 20 minutes, followed by finishing into a prescribed size for sample.

The test items, samples sizes and masurement conditions are tabulated below.

| Test Item | Sample Size | Measurement Condition |
|---|---|---|
| Compressive Strength | 4ϕ × 8 mm | crosshead speed: 2.5 mm/min |
| Bending Strength | 4ϕ × 25 mm | span length: 20 mm, crosshead speed: 1 mm/min |
| Knoop Hardness | 4ϕ × 2 mm | load: 10 g, loading time: 30 seconds |
| Water Sorption | 6ϕ × 1 mm | after 7 days (at 37° C.) |
| Abrasion Wear by Brushing | 10ϕ × 3 mm | load: 2 kg, after 100,000 reciprocations |

Each of the Examples is specifically described below, and the physical properties of each Example are given in Tables A to C. However, it is, as a matter of course, not to be construed that the present invention is limited thereto.

EXAMPLE A-1

A formulation solution having the following composition was used.

| Methyl Methacrylate: | 99 parts |
|---|---|
| Si—P (I/II = 1/99)*: | 1 part |

*The expression "Si—P" is an abbreviation for siloxane polymer; "I" means α-methacryloxypropyl trimethoxysilane and "II" means phenyl triethoxysilane; and the numeral given herein means a molar proportion of I to II (hereinafter the same).

EXAMPLE A-2

A formulation solution having the following composition was used.

| Methyl Methacrylate: | 90 parts |
|---|---|
| Si—P (I/II = 1/99): | 10 parts |

EXAMPLE A-3

A formulation solution having the following composition was used.

| Methyl Methacrylate: | 50 parts |
|---|---|
| Si—P (I/II = 1/99): | 50 parts |

EXAMPLE A-4

A formulation solution having the following composition was used.

| Methyl Methacrylate: | 99 parts |
|---|---|
| Si—P (I/II = 20/80): | 1 part |

EXAMPLE A-5

A formulation solution having the following composition was used.

| Methyl Methacrylate: | 90 parts |
|---|---|
| Si—P (I/II = 20/80): | 10 parts |

EXAMPLE A-6

A formulation solution having the following composition was used.

| Methyl Methacrylate: | 50 parts |
| Si—P (I/II = 20/80): | 50 parts |

EXAMPLE A-7

A formulation solution having the following composition was used.

| Methyl Methacrylate: | 99 parts |
| Si—P (I/II = 50/50): | 1 part |

EXAMPLE A-8

A formulation solution having the following composition was used.

| Methyl Methacrylate: | 90 parts |
| Si—P (I/II = 50/50): | 10 parts |

EXAMPLE A-9

A formulation solution having the following composition was used.

| Methyl Methacrylate: | 50 parts |
| Si—P (I/II = 50/50): | 50 parts |

EXAMPLE A-10

A formulation solution having the following composition was used

| Methyl Methacrylate: | 85 parts |
| Si—P (I/II = 20/80): | 10 parts |
| Ethylene Glycol Dimethacrylate: | 5 parts |

COMPARATIVE EXAMPLE A-11

Only methyl methacrylate was used.

COMPARATIVE EXAMPLE A-12

A formulation solution having the following composition was used.

| Methyl Methacrylate: | 95 parts |
| Ethylene Glycol Dimethacrylate: | 5 parts |

EXAMPLE B-1

A formulation solution having the following composition was used.

| Methyl Methacrylate: | 99 parts |
| Si—P (I/II = 1/99): | 1 part |
| Dimethyl-p-toluidine: | 2 parts |

EXAMPLE B-2

A formulation solution having the following composition was used.

| Methyl Methacrylate: | 90 parts |
| Si—P (I/II = 1/99): | 10 parts |
| Dimethyl-p-toluidine: | 2 parts |

EXAMPLE B-3

A formulation solution having the following composition was used.

| Methyl Methacrylate: | 50 parts |
| Si—P (I/II = 1/99): | 50 parts |
| Dimethyl-p-toluidine: | 2 parts |

EXAMPLE B-4

A formulation solution having the following composition was used.

| Methyl Methacrylate: | 99 parts |
| Si—P (I/II = 20/80): | 1 part |
| Dimethyl-p-toluidine: | 2 parts |

EXAMPLE B-5

A formulation solution having the following composition was used.

| Methyl Methacrylate: | 90 parts |
| Si—P (I/II = 20/80): | 10 parts |
| Dimethyl-p-toluidine: | 2 parts |

EXAMPLE B-6

A formulation solution having the following composition was used.

| Methyl Methacrylate: | 50 parts |
| Si—P (I/II = 20/80): | 50 parts |
| Dimethyl-p-toluidine: | 2 parts |

EXAMPLE B-7

A formulation solution having the following composition was used.

| Methyl Methacrylate: | 99 parts |
| Si—P (I/II = 50/50): | 1 part |
| Dimethyl-p-toluidine: | 2 parts |

EXAMPLE B-8

A formulation solution having the following composition was used.

| Methyl Methacrylate: | 90 parts |
| Si—P (I/II = 50/50): | 10 parts |
| Dimethyl-p-toluidine: | 2 parts |

EXAMPLE B-9

A formulation solution having the following composition was used.

| | |
|---|---|
| Methyl Methacrylate: | 50 parts |
| Si—P (I/II = 50/50): | 50 parts |
| Dimethyl-p-toluidine: | 2 parts |

EXAMPLE B-10

A formulation solution having the following composition was used.

| | |
|---|---|
| Methyl Methacrylate: | 85 parts |
| Si—P (I/II = 20/80): | 10 parts |
| Dimethyl-p-toluidine: | 2 parts |
| Ethylene Glycol Dimethacrylate: | 5 parts |

COMPARATIVE EXAMPLE B-11

A formulation solution having the following composition was used.

| | |
|---|---|
| Methyl Methacrylate: | 100 parts |
| Dimethyl-p-toluidine: | 2 parts |

COMPARATIVE EXAMPLE B-12

A formulation solution having the following composition was used.

| | |
|---|---|
| Methyl Methacrylate: | 95 parts |
| Ethylene Glycol Dimethacrylate: | 5 parts |
| Dimethyl-p-toluidine: | 2 parts |

EXAMPLE C-1

A formulation solution having the following composition was used.

| | |
|---|---|
| D-2.6E*: | 99 parts |
| Si—P (I/II = 1/99): | 1 part |

*The expression "D-2.6E" is an abbreviation for 2,2-bis(4-methacryloxypolyethoxyphenyl)propane to which 2.6 moles in average of ethylene oxide is adducted.

EXAMPLE C-2

A formulation solution having the following composition was used.

| | |
|---|---|
| D-2.6E: | 90 parts |
| Si—P (I/II = 1/99): | 10 parts |

EXAMPLE C-3

A formulation solution having the following composition was used.

| | |
|---|---|
| D-2.6E: | 80 parts |
| Si—P (I/II = 1/99): | 20 parts |

EXAMPLE C-4

A formulation solution having the following composition was used.

| | |
|---|---|
| D-2.6E: | 99 parts |
| Si—P (I/II = 20/80): | 1 part |

EXAMPLE C-5

A formulation solution having the following composition was used.

| | |
|---|---|
| D-2.6E: | 90 parts |
| Si—P (I/II = 20/80): | 10 parts |

EXAMPLE C-6

A formulation solution having the following composition was used.

| | |
|---|---|
| D-2.6E: | 80 parts |
| Si—P (I/II = 20/80): | 20 parts |

EXAMPLE C-7

A formulation solution having the following composition was used.

| | |
|---|---|
| D-2.6E: | 99 parts |
| Si—P (I/II = 50/50): | 1 part |

EXAMPLE C-8

A formulation solution having the following composition was used.

| | |
|---|---|
| D-2.6E: | 90 parts |
| Si—P (I/II = 50/50) | 10 parts |

EXAMPLE C-9

A formulation solution having the following composition was used.

| | |
|---|---|
| D-2.6E: | 80 parts |
| Si—P (I/II = 50/50): | 20 parts |

COMPARATIVE EXAMPLE C-10

Only D-2.6E was used.

TABLE A

| (1) | (2) | (3) | (4) | (5) | (6) |
|---|---|---|---|---|---|
| A-1 | 1270 | 1811 | 19.6 | 0.53 | 12.2 |
| A-2 | 1332 | 1831 | 20.0 | 0.53 | 11.1 |
| A-3 | 1415 | 1795 | 20.3 | 0.45 | 10.9 |
| A-4 | 1301 | 1843 | 19.2 | 0.55 | 12.4 |
| A-5 | 1483 | 2277 | 21.2 | 0.52 | 10.5 |
| A-6 | 1491 | 1876 | 21.6 | 0.40 | 10.0 |
| A-7 | 1235 | 1833 | 19.0 | 0.55 | 12.4 |
| A-8 | 1515 | 2247 | 21.3 | 0.50 | 10.1 |
| A-9 | 1501 | 1881 | 21.4 | 0.46 | 9.9 |
| A-10 | 1487 | 1820 | 21.5 | 0.47 | 10.0 |
| A-11 | 1165 | 1682 | 18.1 | 0.65 | 13.2 |

TABLE A-continued

| (1) | (2) | (3) | (4) | (5) | (6) |
|---|---|---|---|---|---|
| A-12 | 1203 | 1598 | 18.3 | 0.67 | 12.2 |

(1): Example and Comparative Example No.
(2): Compressive Strength (kg/cm$^2$)
(3): Bending Strength (kg/cm$^2$)
(4): Knoop Hardness (K.H.N.)
(5): Water Sorption (mg/cm$^2$)
(6): Abrasion Wear by Brushing ($\times 10^{-3}$ mm)

TABLE B

| (1) | (2) | (3) | (4) | (5) | (6) |
|---|---|---|---|---|---|
| B-1 | 900 | 1584 | 15.1 | 0.67 | 14.8 |
| B-2 | 909 | 1712 | 16.1 | 0.65 | 13.9 |
| B-3 | 1012 | 1719 | 16.2 | 0.61 | 13.6 |
| B-4 | 918 | 1604 | 15.6 | 0.70 | 15.5 |
| B-5 | 1013 | 1870 | 16.8 | 0.66 | 13.9 |
| B-6 | 1069 | 1898 | 16.9 | 0.60 | 13.7 |
| B-7 | 895 | 1574 | 15.5 | 0.70 | 15.4 |
| B-8 | 1077 | 1802 | 17.2 | 0.67 | 14.2 |
| B-9 | 1065 | 1830 | 17.4 | 0.59 | 13.8 |
| B-10 | 1022 | 1753 | 17.3 | 0.61 | 14.0 |
| B-11 | 816 | 1491 | 14.3 | 0.80 | 16.1 |
| B-12 | 861 | 1422 | 15.0 | 0.83 | 15.8 |

(1): Example and Comparative Example No.
(2): Compressive Strength (kg/cm$^2$)
(3): Bending Strength (kg/cm$^2$)
(4): Knoop Hardness (K.H.N.)
(5): Water Sorption (mg/cm$^2$)
(6): Abrasion Wear by Brushing ($\times 10^{-3}$ mm)

TABLE C

| (1) | (2) | (3) | (4) | (5) | (6) |
|---|---|---|---|---|---|
| C-1 | 1067 | 1261 | 20.8 | 0.35 | 10.5 |
| C-2 | 1098 | 1282 | 21.1 | 0.33 | 9.8 |
| C-3 | 1175 | 1373 | 21.3 | 0.29 | 9.6 |
| C-4 | 1094 | 1275 | 20.8 | 0.36 | 10.8 |
| C-5 | 1242 | 1421 | 21.3 | 0.35 | 10.2 |
| C-6 | 1247 | 1416 | 21.4 | 0.30 | 10.1 |
| C-7 | 1042 | 1300 | 20.9 | 0.35 | 10.5 |
| C-8 | 1265 | 1476 | 21.2 | 0.30 | 10.1 |
| C-9 | 1256 | 1465 | 21.4 | 0.29 | 9.8 |
| C-10 | 960 | 1252 | 19.8 | 0.40 | 11.4 |

(1): Example and Comparative Example NO.
(2): Compressive Strength (kg/cm$^2$)
(3): Bending Strength (kg/cm$^2$)
(4): Knoop Hardness (K.H.N.)
(5): Water Sorption (mg/cm$^2$)
(6): Abrasion Wear by Brushing ($\times 10^{-3}$ mm)

It is clear from the foregoing results that the dental resin composition of the present invention comprising a siloxane polymer having a stiff ladder structure and having a polymerizable ethylenically unsaturated group and a hydrophobic group in the side chain of the same molecule thereof and an Si—O bond in the main chain thereof can markedly improve the physical properties without impairing any inherent advantages of the methyl methacrylate-based material.

In the polymer comprising the resin composition in accordance with the present invention, since the siloxane polymer has a stiff ladder structure and has a polymerizable functional group, it is improved in the hardness and compressive strength and is excellent particularly in the bending strength, and therefore, it can not only prevent the breakage found in the conventional denture base resin but also make the denture thinner.

In addition, when the resin composition of the present invention is used as a crown and bridge resin, it can be improved in abrasion wear and breakage of the incisal edge Further, the resin composition of the present invention has a hydrophobic group in the side chain thereof, it can form a prosthetic appliance having a less water sorption and be found to have an effect to prevent the discoloration and coloring material decomposition in the oral conditions.

While the invention has been described in detail and with reference to specific embodiments thereof, it will be apparent to one skilled in the art that various changes and modifications can be made therein without departing from the spirit and scope thereof.

What is claimed is:

1. A dental resin comprising:
   (a) a siloxane polymer produced by polymerizing an oligomer, said oligomer consisting essentially of:
      (i) at least one silane compound of the formula:

$$A-R_c-Si-D_3 \qquad (I)$$

wherein D is a hydrolyzable group, R is a $C_1$–$C_4$ alkylene group, c is an integer of 0 or 1, and A represents a group of the formula:

$$CH_2=CH- \quad \text{or} \quad CH_2=\overset{X}{\underset{|}{C}}-\overset{O}{\underset{\|}{C}}-O-$$

wherein X is a hydrogen atom or a $C_1$–$C_6$ alkyl group; and
      (ii) at least one silane compound of the formula:

$$A'-Si-D_3 \qquad (II)$$

wherein D is a hydrolyzable group and A' is a phenyl group or a $C_1$–$C_9$ alkyl group, and wherein said oligomer is produced under conditions such that hydrolysis of the silane compounds is effected;
   (b) a monomer copolymerizable with said siloxane polymer; and
   (c) a polymerization catalyst; and wherein said siloxane polymer (a) is at least one member selected from the group consisting of those obtained by polymerizing an oligomer comprising from 1 to 50 mol % of said silane compound of the formula (I) having bonded thereto from 50 to 99 mol % of said silane compound having the formula (II); and further wherein said dental resin comprises from 1 to 50% by wt. of said siloxane polymer (a) and from 50 to 99% by wt. of said monomer (b).

2. The dental resin composition as claimed in claim 1, wherein said monomer (b) is at least one member of acrylic acid ester-based compounds and methacrylic acid esterbased compounds.

3. The dental resin composition as claimed in claim 1, wherein said polymerization catalyst (c) is comprised of an organic peroxide.

4. The dental resin composition as claimed in claim 1, wherein said polymerization catalyst (c) is comprised of an organic peroxide and a tertiary amine, maintained in such a state that both are not brought into contact with each other, and at the initiation of the polymerization, a composition having said organic peroxide added thereto is mixed for use with a composition having said tertiary amine added thereto.

5. The dental resin composition as claimed in claim 3, wherein the amount of said organic peroxide added is from 0.1 to 5% by weight.

6. The dental resin composition as claimed in claim 8, wherein the amount of said tertiary amine added is from 0.5 to 5% by weight.

7. A dental resin composition comprising:

(a) a siloxane polymer produced by polymerizing an oligomer, said oligomer consisting essentially of:
(i) at least one silane compound of the formula:

$$A-R_c-Si-D_3 \qquad (I)$$

wherein D is a hydrolyzable group, R is a $C_1$-$C_4$ alkylene group, c is an integer of 0 or 1, and A represents a group of the formula:

$$CH_2=CH- \text{ or } CH_2=\overset{X}{\underset{|}{C}}-\overset{O}{\underset{\|}{C}}-O-$$

wherein X is a hydrogen atom or a $C_1$-$C_6$ alkyl group; and
(ii) at least one silane compound of the formula:

$$A'-Si-D_3 \qquad (II)$$

wherein D is a hydrolyzable group and A' is a phenyl group or a $C_1$-$C_9$ alkyl group, and wherein the oligomer is produced under conditions such that hydrolysis of the silane compounds is effected;
(b) a monomer copolymerizable with said siloxane polymer;
(c) a polymerization catalyst; and
(d) a filler; and wherein said siloxane polymer (a) is at least one member selected from the group consisting of those obtained by polymerizing an oligomer comprising 1 to 50 mol % of said silane compound of the formula (I) having bonded thereto from 50 to 99 mol % of said silane compound having the formula (II); and further wherein said dental resin comprises from 1 to 50% by wt. of said siloxane polymer (a) and from 50 to 99% by wt. of said monomer (b).

8. The dental resin composition as claimed in claim 7, wherein said monomer (b) is at least one member of acrylic acid ester-based compounds and methacrylic acid ester-based compound.

9. The dental resin composition as claimed in claim 7, wherein said polymerization catalyst (c) is comprised of an organic peroxide.

10. The dental resin composition as claimed in claim 7, wherein said polymerization catalyst (c) is comprised of an organic peroxide and a tertiary amine, maintained in such a state that the both are not brought into contact with each other, and at the initiation of the polymerization, a composition having said organic peroxide added thereto is mixed for use with a composition having said tertiary amine added thereto.

11. The resin composition as claimed in claim 9, wherein the amount of said organic peroxide added is from 0.1 to 5% by weight.

12. The dental resin composition as claimed in claim 10, wherein the amount of said tertiary amine added is from 0.5 to 5% by weight.

13. The dental resin composition as claimed in claim 7, wherein said filler (d) is comprised of an inorganic filler and/or an organic filler.

14. The dental resin composition as claimed in claim 7, wherein said filler (d) is mixed in an amount from 1 to 80% by weight.

15. The dental resin composition as claimed in claim 1, wherein said hydrolyzable group D in both silane compounds is a hydrolyzable group selected from the group consisting of chloro, methoxy, ethoxy, propoxy and isopropoxy.

16. The dental resin composition as claimed in claim 1, wherein said hydrolysis conditions comprise adding to said silane compounds tetrahydrofuran, hydrochloric acid and water.

17. The dental resin composition as claimed in claim 7, wherein said hydrolysis conditions comprise adding to said silane compounds tetrahydrofuran, hydrochloric acid and water.

18. The dental resin composition as claimed in claim 7, wherein said hydrolyzable group D in both silane compounds is a hydrolyzable group selected from the group consisting of chloro, methoxy, ethoxy, propoxy and isopropoxy.

19. The dental resin composition as claimed in claim 1, wherein said silane compound (I) is selected from the group consisting of γ-methacryloxypropyl trimethoxysilane, γ-methacryloxypropyl triethoxysilane, vinyl triethoxysilane, vinyl tris (β-methoxyethoxy) silane and vinyl trichlorosilane.

20. The dentral resin composition as claimed in claim 1, wherein the silane compound (II) is selected from the group consisting of phenyl trimethoxysilane, phenyl triethoxysilane, methyl trimethoxysilane, ethyl trimethoxysilane, n-propyl trimethoxysilane, n-butyl trimethoxysilane, phenyl trichlorosilane, methyl trichlorosilane, ethyl trichlorosilane, n-propyl trichlorosilane and n-butyl trichlorosilane.

21. The dental resin composition as claimed in claim 7, wherein said silane compound (I) is selected from the group consisting of γ-methacryloxypropyl trimethoxysilane, γ-methacryloxypropyl triethoxysilane, vinyl triethoxysilane, vinyl tris (β-methoxyethoxy) silane and vinyl trichlorosilane.

22. The dental resin composition as claimed in claim 7, wherein said silane compound (II) is selected from the group consisting of phenyl trimethoxysilane, phenyl triethoxysilane, methyl trimethoxysilane, ethyl trimethoxy-silane, n-propyl trimethoxysilane, n-butyl trimethoxysilane, phenyl trichlorisilane, methyl trichlorosilane, ethyl trichlorosilane, n-propyl trichlorosilane and n-butyl trichlorosilane.

* * * * *